United States Patent [19]

Österberg et al.

[11] Patent Number: 5,962,650
[45] Date of Patent: *Oct. 5, 1999

[54] OXYGEN-REDUCED AQUEOUS SOLUTION OF FACTOR VIII

[75] Inventors: Thomas Österberg; Angelica Fatouros, both of Stockholm, Sweden

[73] Assignee: Pharmacia & Upjohn Aktiebolag, Stockholm, Sweden

[*] Notice: This patent issued on a continued prosecution application filed under 37 CFR 1.53(d), and is subject to the twenty year patent term provisions of 35 U.S.C. 154(a)(2).

[21] Appl. No.: 08/535,251

[22] PCT Filed: Mar. 24, 1994

[86] PCT No.: PCT/SE94/00265

§ 371 Date: Oct. 30, 1995

§ 102(e) Date: Oct. 30, 1995

[87] PCT Pub. No.: WO94/26286

PCT Pub. Date: Nov. 24, 1994

[30] Foreign Application Priority Data

May 7, 1993 [SE] Sweden .................................. 9301581

[51] Int. Cl.⁶ .................................................. A61K 35/14
[52] U.S. Cl. ................................ 530/383; 514/2; 514/21; 424/529; 424/530
[58] Field of Search ...................... 424/529, 530; 435/2; 530/383; 514/2.21

[56] References Cited

U.S. PATENT DOCUMENTS

| | | | |
|---|---|---|---|
| 2,896,381 | 7/1959 | Lange | 53/426 |
| 3,143,471 | 8/1964 | Coady | 53/432 |
| 4,165,370 | 8/1979 | Coval | 424/85 |
| 4,597,966 | 7/1986 | Zolton et al. | 424/85 |
| 4,709,819 | 12/1987 | Lattuada et al. | 206/524.8 |
| 4,727,027 | 2/1988 | Wiesehahn et al. | 435/173 |
| 4,783,441 | 11/1988 | Thurow | 514/3 |
| 4,877,608 | 10/1989 | Lee et al. | 424/85 |
| 5,118,794 | 6/1992 | Grangeorge et al. | 530/363 |
| 5,328,694 | 7/1994 | Schwinn | 424/423 |

FOREIGN PATENT DOCUMENTS

| | | |
|---|---|---|
| 0 078 961 A2 | of 1983 | European Pat. Off. . |
| 0 078 961 A2/A3 | of 1983 | European Pat. Off. . |
| 0 099 445 A2 | of 1984 | European Pat. Off. . |
| 0 212 040 A1 | of 1987 | European Pat. Off. . |
| 0 268 110 A1 | of 1988 | European Pat. Off. . |
| 0 314 095 B1 | of 1989 | European Pat. Off. . |
| 0 315 968 B1 | of 1992 | European Pat. Off. . |
| 0 508 194 A1 | of 1992 | European Pat. Off. . |
| WO 89/09614 | of 1989 | WIPO . |
| WO 89/09615 | of 1989 | WIPO . |
| WO 91/09122 | of 1991 | WIPO . |
| WO 91/10439 | of 1991 | WIPO . |

OTHER PUBLICATIONS

Wood et al., Expression of active human factor VIII from combinant DNA clones, Articles, Nature, vol. 312, Nov., 1984, pp. 330–337.

Andersson et al., Isolation and characterization of human factor VIII: Molecular forms in commercial factor VIII concentrate, cryoprecipitate, and plasma, Proc. Natl. Acad. Sci., USA, vol. 83, May, 1986, pp. 1979–1983.

Wan et al., CYM of Polysorbates, Journal of Pharmaceutical Sciences, vol. 63, No. 1, Jan., 1974, pp. 136–137.

Shaw, Introduction to Colloid and Surface Chemistry, Liquid–Gas and Liquid–Liquid Interfaces, Butterworths, 1970, pp. 71–73.

*Primary Examiner*—Jean C. Witz
*Attorney, Agent, or Firm*—Pollock, Vande Sande & Amernick

[57] ABSTRACT

The present invention relates to a final drug product comprising coagulation factor VIII in an aqueous solution with a reduced concentration of oxygen. In this way, the factor VIII activity can be retained during storage to a surprisingly high degree. The factor VIII activity can be retained for a prolonged period of time, if the final drug product further comprises an inert gas and/or an antioxidant. The present invention also relates to processes for reducing the oxygen concentration of the aqueous solution, and a method for improving the stability of factor VIII in an aqueous solution by storing the solution under an inert gas atmosphere. By the present invention it is possible to retain at least 50% of the initial activity of factor VIII after storage for at least 6 months at a temperature of 2 to 10° C. and a pH of the solution of 6.5 to 8.5.

16 Claims, No Drawings

ОXYGEN-REDUCED AQUEOUS SOLUTION OF FACTOR VIII

The present invention relates to a final drug product comprising coagulation factor VIII in an aqueous solution with a reduced concentration of oxygen. In this way, the factor VIII activity can be retained during storage to a surprisingly high degree. The factor VIII activity can be retained for a prolonged period of time, if the final drug product further comprises an inert gas and/or an antioxidant. The present invention also relates to processes for reducing the oxygen concentration of the aqueous solution, and a method for improving the stability of factor VIII in an aqueous solution by storing the solution under an inert gas atmosphere. By the present invention it is possible to retain at least 50% of the initial activity of factor VIII after storage for at least 6 months at a temperature of 2 to 10° C. and a pH of the solution of 6.5 to 8.5.

BACKGROUND OF THE INVENTION

The stability of proteins is generally a problem in pharmaceutical industry. It has often been solved by drying the protein in various drying processes, such as freeze-drying. The protein has thereafter been distributed and stored in dried form. The solution before drying or freeze-drying, the dried material and the reconstituted product should all be stable, to avoid a substantial loss of activity in the drying process, as well as during storage or handling. The freeze-drying process is a costly and time consuming process step, and it would be of great advantage if this step could be avoided, when preparing a commercial product. Furthermore, the patient necessarily has to reconstitute the dried protein in a solvent before use, which could be inconvenient for the patient.

Haemophilia is an inherited disease which has been known for centuries but it is only within the last three decades that it has been possible to differentiate between the various forms; haemophilia A, haemophilia B and haemophilia C. Haemophilia A is the most frequent form. It affects only males with an incidence of one or two individuals per 10 000 live-born males. The disease is caused by strongly decreased level or absence of biologically active coagulation factor VIII (antihaemophilic factor) which is a protein normally present in plasma. The clinical manifestation of haemophilia A is a strong bleeding tendency and before treatment with factor VIII concentrates was introduced, the mean age of those patients was less than 20 years. Concentrates of factor VIII obtained from plasma have been available for about three decades. This has improved the situation for treatment of haemophilia patients considerably and given them possibility to live a normal life.

Therapeutic factor VIII concentrates have until now been prepared by fractionation of plasma. However, there are now methods available for production of factor VIII in cell culture using recombinant DNA techniques as reported in e.g. J Gitschier et al. Nature 312, p. 330–37, 1984 and EP-A-160 457.

Factor VIII concentrates derived from human plasma contain several fragmented fully active factor VIII forms (Andersson et al, Proc. Natl. Acad. Sci. USA, Vol 83, p. 2979–83, May 1986). The smallest active form has a molecular mass of 170 kDa and consists of two chains of 90 kDa and 80 kDa held together by a metal ion bridge. Reference is here made to EP-A-1 97 901.

Kabi Pharmacia has developed a recombinant factor VIII product which corresponds to the 170 kDa plasma factor VIII form in therapeutic factor VIII concentrates. The truncated recombinant factor VIII molecule is termed r-VIII SQ and is produced by Chinese Hamster Ovary (CHO) cells in a cell culture process in serum free medium at finite passage.

The specific activity of r-VIII SQ is about 15 000 IU VIII:C per mg protein.

Recombinant factor VIII SQ is indicated for treatment of classical haemophilia. The dosage is similar to the dosage of the plasma factor VIII concentrates.

The structure and biochemistry of recombinant factor VIII-products in general have been described by Kaufman in Tibtech, Vol 9,1991 and Hematology, 63, p. 155–65, 1991. The structure and biochemistry of r-VIII SQ have been descrbed in WO-A-91/09122.

Factor VIII which has been fractionated from plasma is normally sold as freeze-dried powder which should be reconstituted with water.

A formulation with a low amount of protein will generally loose activity during purification, sterile manufacturing, in the package and during administration. This problem is usually solved by the addition of human albumin which reduces the loss of the active protein considerably. Human albumin functions as a general stabiliser during purificationa, sterile manufacturing and freeze-drying (see review by Wang et al., J. of Parenteral Sci. and Tech. Vol 42, Number 2S, supplement. 1988). The use of albumin for stabilisation of factor VIII is known and is currently used in all highly purified factor VIII products on the market.

However, it is desirable to avoid addition of human albumin to a therapeutic protein manufactured by recombinant DNA technology. In addition, the use of human albumin as a formulation excipient often limits the use of many of the most powerful and sensitive analytical methods for protein characterisation.

Several solutions have been proposed for stabilisation of different proteins. Thus, EP 35 204 (Cutter) discloses a method for imparting thermal stability to a protein composition in the presence of a polyol. Furthermore, WO-A-89/09614 (Genentech) discloses a stabilised formulation of human growth hormone comprising glycine, mannitol and a buffer is disclosed and in a preferred embodiment a non-ionic surfactant such as polysorbate 80 is added. The non-ionic surfactant is added for reduced aggregation and denaturation. The formulation has an increased stability in a freeze-dried formulation and upon reconstitution. Also, U.S. Pat. No. 4,783,441 (Hoechst) discloses an aqueous solution comprising a protein, such as insulin and a surface active substance.

EP 77 870 (Green Cross) discloses the addition of amino acids, monosaccharides, oligo-saceharides or sugar alcohols or hydrocarbon carboxylic acid to improve stability of a solution containing factor VIII. EP 117 064 (Green Cross) discloses the addition of sugar alcohol or disaccharides to an aqueous solution of factor VIII for increasing the stability during heat treatment.

WO-A-91/10439 (Octapharma) claims stable injectable solution of factor VIII or factor IX which comprises a disaccharide, preferably saccarose and one or more amino acids and EP 315 968 and EP 314 095 (Rorer) claim stable formulations of factor VIII with different ionic strength.

U.S. Pat. No. 4,727,027 (Diamond Scientific) is directed to a method for photochemical decontamination of aqueous compositions containing biologically active proteins derived from blood or blood components, for minimizing loss in activity. The method comprises adding at least one furocoumarin to the composition and irradiating the obtained composition with ultraviolet (UV) light. Prior to the irradiation, the oxygen concentration of the aqueous composition can be reduced to inhibit denaturation. This can be achieved, e.g. by addition of oxygen scavengers, albumins and/or enzyme systems and/or flushing with an inert gas. Solutions containing factor VIII were flushed with argon with or without ascorbate for up to 6 hours. U.S. Pat. No. 4,727,027 is silent about storage of solutions for a prolonged time, as well as the possible effect of reduced oxygen concentration on factor VIII activity in such storage.

EP-A-0 212 040 (Immuno) relates to virus inactivation of factor VIII by heating of dry substance in an oxygen reduced environment. The heat treatment is carried out in the absence of stabilisers, since the latter protects also the viruses thereby reducing the efficiency of the treatment. Tests are carried out at 90° C. for 30 hours. EP-A-0 212 040 is silent about the problem of poor stability of aqueous solutions containing factor VIII, which generally is a much more difficult problem to overcome than poor stability of dry products. This is because chemical changes, e.g. hydrolysis and deamidation, are much more pronounced in a solution than in the dry state.

Proteins are different with regard to physio-chemical properties. When preparing a pharmaceutical preparation which should be physiologically acceptable, and stable for a long time, consideration can not only be taken to the properties of the protein but also other aspects must be considered. Examples of the latter, are the industrial manufacture, as well as ease of handling and safety for the patient. The consequences of these aspects are not predictable when testing different formulations and there is often a unique solution for each protein.

It would facilitate the use and manufacture of factor VIII if the protein could be formulated and distributed to the patient as a stable solution without the addition of albumin and with a prolonged storage life. Also for the patient such a solution would facilitate the handling of the final drug product. The patient could thus inject the content of the final drug product directly without reconstitution.

Aqueous solutions containing oxygen-sensitive chemical compounds including drugs other than proteins, could be deoxygenated as follows:
  Water for injection is bubbled with nitrogen to reduce the concentration of oxygen.
  The components are dissolved and the solution is bubbled with nitrogen and thereafter kept under a nitrogen blanket. During filling, the bottles are flushed with nitrogen gas and the bottles are closed under a stream of nitrogen.

It is, however, not possible to deoxygenate a protein solution by bubbling the solution with a gas. Protein solutions will foam heavily and many protein drugs, such as coagulation factor VIII, will denature if exposed to such a treatment. Therefore, it has never been suggested earlier that an aqueous solution containing coagulation factor VIII should be stored under an inert gas such as nitrogen.

DESCRIPTION OF THE INVENTION

However, we have found that solutions containing coagulation factor VIII can be deoxygenated without protein denaturation. Thus, to our great surprise we have found that coagulation factor VIII can be stabilised without albumin, and that such an aqueous solution with a low oxygen content is stable when stored at e.g. 2–8° C.

Thus the present invention relates to a final drug product comprising coagulation factor VIII in an aqueous solution with a reduced concentration of oxygen, for essentially retaining the factor VIII activity during storage.

Factor VIII can either be plasma factor VIII or recombinant factor VIII. When factor VIII is recombinant it can be either in its full-length form or preferably a deletion derivative thereof. More preferably, the deletion derivative is recombinant deletion derivative FVIII SQ (r-VIII SQ). The factor VIII activity can be from 10 to 100,000 IU/ml, preferably from 50 to 10,000 IU/ml.

Factor VIII used in the examples is highly purified, i.e. has a specific activity of more than 5000 IU/mg protein, and the composition according to the invention is stabilised without the addition of albumin.

The concentration of oxygen can be reduced either by subjecting the aqueous solution to an inert gas atmosphere, or by first reducing the pressure and thereafter introducing the inert gas. The latter process is preferably repeated in several cycles. By this method the oxygen content in the solution can be reduced to a low level, without a substantial loss in factor VIII activity. The oxygen content in the solution can be below 200 ppm, suitably below 50 ppm, preferably below 10 ppm and more preferably below 2 ppm. The content of oxygen in the container used can be reduced in the same way, preferably by subjecting the container to an inert gas atmosphere.

Final drug product relates to the formulated drug in its final container. Suitable containers in the present invention are e.g. vials, syringes and injection devices.

The solution is suitably stored under an inert gas such as nitrogen, argon or helium, to essentially maintain the low content of oxygen. The inert gas is preferably a non-noble inert gas, and more preferably nitrogen.

The low content of oxygen can also be essentially maintained by adding an antioxidant to the aqueous solution. Thus, preferably, the solution further contains at least one antioxidant, such as glutathione, acetylcysteine, methionine, tocopherol, butyl hydroxy toluene, butyl hydroxy anisole or phenolic compounds. Preferably, the antioxidant is at least one compound selected from the group consisting of glutathione, acetylcysteine and methionine. Complexing agents, such as EDTA and citric acid, can further improve the stability of factor VIII.

The amount of the antioxidant depends on the compound used. Therefore, no concentration or amount can generally be given. It is, however, important that the amount of antioxidant, if used, is in a pharmaceutically acceptable amount.

The pH of the solution is suitably 6.5 to 8.5 and preferably about 7.

A non-ionic surfactant is preferably present in the solution. The non-ionic surfactant, if present, is preferably chosen from block co-polymers such as a poloxamer or polyoxyethylene sorbitan fatty acid ester, such as polysorbate 20 or polysorbate 80. The non-ionic surfactant should, if present, be used in an amount above the critical micelle concentration (CMC). See Wan and Lee, Journal of Pharm Sci, 63, p. 136, 1974. The polyoxyethylene sorbitan fatty acid ester is thus preferably used in an amount of at least 0.01 mg/ml.

The aqueous solution can further contain sodium or potassium chloride, preferably in an amount of more than 0.1 M.

The association of the heavy and light chains of factor VIII, is dependent on the presence of calcium (or other divalent metal ions). Here calcium was added as calcium chloride ($CaCl_2$), but other salts such as calcium gluconate, calcium glubionate or calcium gluceptate can also be used, preferably in an amount of more than 0.5 mM.

The aqueous solution suitably contains an amino acid, such as L-histidine, lysine and/or arginine, in an amount of more than 1 mM. Mono- or disaccharides such as sucrose or sugar alcohols could be added. Preferably, the solution contains L-histidine and sucrose.

The final drug product preferably comprises an aqueous solution containing i) 10–100000 IU/ml of recombinant coagulation factor VIII ii) at least 0.01 mg/ml of a polyoxyethylene sorbitan fatty acid ester iii) sodium chloride, preferably in an amount of more than 0.1M.

iv) calcium salt, such as calcium chloride or calcium gluconate, preferably in an amount of more than 0.5 mM.

v) an amino acid, such as L-histidine, in an amount of more than 1 mM.

vi) a mono- or disaccharide or a sugar alcohol, preferably sucrose or mannitol

To this solution could an antioxidant in a pharmaceutically acceptable amount be added.

The final drug product thus comprises a stable aqueous solution ready for use.

The claimed solution can be prepared by a process, where the coagulation factor VIII is mixed with an aqueous solution, or where the coagulation factor VIII is eluted from the last purification step with an aqueous solution. The aqueous solution, suitably contains at least one additive selected from the group consisting of a non-ionic surfactant, an antioxidant, an amino acid such as L-histidine, sodium salt, a calcium salt and sucrose.

The invention also relates to a method for improving the stability of coagulation factor VIII in an aqueous solution, whereby the solution is stored under an inert gas atmosphere. The invention further relates to a method whereby it is possible to retain at least 50%, and even 80%, of the initial factor VIII activity after storage for at least 6 months at a temperature of 2 to 10° C. and a pH of the solution of 6.5 to 8.5. By using the present invention it is possible to store the final drug product comprising factor VIII in an aqueous solution for 12 and even 24 months, without appreciable loss of factor VIII activity. The method is particularly applicable when factor VIII is r-VIII SQ, since the data presented in the examples indicate that r-VIII SQ is essentially stable for at least 6 months when stored under nitrogen at 5±30° C.

The following examples illustrate the invention and show stability data for different aqueous solutions, when subjected to treatment in nitrogen and argon according to the invention and in air for comparison. The patent protection is not limited to these examples.

EXPERIMENTAL

Material and Methods

The production of recombinant factor VIII SO (r-VIII SQ) was essentially performed as described in patent WO-A-91/09122, example 1–3. A DHFR deficient CHO celline (DG44N.Y.) was electroporated with an expression vector containing the r-VIII SQ gene and an expression vector containing the dihydrofolate-reductase gene. Following selection on selective media surviving colonies were amplified through growth in stepwise increasing amounts of methotrexate. Supernatant from the resulting colonies were individually screened for factor VIII activity. A production clone was chosen and this was subsequently adapted to serum-free suspension growth in a defined medium and finally a large scale fermentation process was developed. Supernatant is collected after certain time periods and further purified as described below.

The clarified conditioned medium was pH adjusted and applied to a S-Sepharose FF column. After washing, factor VIII was eluted with a salt buffer containing 5 mM $CaCl_2$.

Immunoadsorption was carried out on an immunoaffinity resin where the ligand was a monoclonal antibody (8A4) directed towards the heavy chain of Factor VIII. Before loading to the column the S-eluate was treated with 0.3% TNBP and 1% Octoxynol 9.

The column was equilibrated, washed and factor VIII was eluated with a buffer containing 0.05M $CaCl_2$ and 50% ethylene glycol.

The mAb-eluate was loaded on a Q-Sepharose FF column, equilibrated with the elution buffer in the immunoaffinity step. After washing, factor VIII was eluated with 0.05 M L-histidine, 4 mM $CaCl_2$, 0.6M NaCl, pH 6.8.

The Q-eluate was applied to a gel filtration column (Superdex 200 p.g.). Equilibration and elution was carried out with a formulation buffer giving the composition according to the examples below.

Bulk material of r-VIII SQ was received from the final purification step. The activity of factor VIII and the concentration of the inactive components were adjusted by diluting with an appropriate buffer. The solution was then sterile filtered (0.22 $\mu$m) and dispensed and deoxygenated by subjecting the solution to reduced pressure and thereafter introducing the inert gas in several cycles.

The activity of coagulation factor VIII was assessed by a chromogenic substrate assay (Coatest Factor VIII, Chromogenix AB, Mölndal, Sweden). Activated factor X (Xa) is generated via the intrinsic pathway where factor VIII acts as cofactor. Factor Xa is then determined by the use of a synthetic chromogenic substrate, S-2222 in the presence of a thrombin inhibitor I-2581 to prevent hydrolysis of the substrate by thrombin. The reaction is stopped with acid, and the VIII:C, which is proportional to the release of pNA (para-nitroaniline), is determined photometrically at 450 nm against a reagent blank. The unit of factor VIII:C is expressed in international units (IU) as defined by the current International Concentrate Standard (IS) established by WHO.

EXAMPLE 1

Comparison Between Solutions Stored Under Air or Nitrogen

Recombinant factor VIII was prepared according to the method described under Experimental. The solutions were stored at three different temperatures, 7, 25° C. and 30° C., respectively.

The dispensed volume in the vials was 2 ml.

TABLE 1

The compositions were the following

|  | 1A | 1B | 1C | 1D | 1E | 1F |
|---|---|---|---|---|---|---|
| L-Histidine, mM | 14.7 | 14.7 | 14.7 | 14.7 | 14.7 | 14.7 |
| Sodium chloride, M | 0.31 | 0.31 | 0.31 | 0.31 | 0.31 | 0.31 |
| Calcium chloride, mM | 3.7 | 3.7 | 3.7 | 3.7 | 3.7 | 3.7 |
| Polysorbate mg/ml | 0.23 | 0.23 | 0.23 | 0.23 | 0.23 | 0.23 |
| pH | 7 | 6 | 7 | 7 | 6 | 7 |

TABLE 1-continued

| | 1A | 1B | 1C | 1D | 1E | 1F |
|---|---|---|---|---|---|---|
| Headspace | $N_2$ | $N_2$ | air | $N_2$ | $N_2$ | air |
| VIII:C IU/ml | | | | | | |
| Initial | 267 | 258 | 267 | 260 | 259 | 260 |
| 3 months, 7° C. | 238 | 219 | — | 224 | 151 | — |
| 6 months, 7° C. | 217 | 186 | 158 | 204 | 84 | 20 |
| 1 months, 25° C. | 220 | — | — | 232 | — | — |
| 3 months, 25° C. | 198 | — | — | 186 | — | — |
| 1 months, 30° C. | 210 | 181 | 136 | 210 | 160 | 8 |
| 3 months, 30° C. | 158 | 126 | 26 | 152 | 54 | 2 |

It is clear from the Example, that the absence of oxygen at 7° C. gives an acceptable recovery of VIII:C after 6 months when stored as a solution. Even at 25 or 30° C. the solution according to the invention can be stored without too much loss of activity. It can further be seen that the stability was better at a pH of 7 than at pH of 6.

EXAMPLE 2

Solutions Containing an Antioxidant and Sucrose.

Recombinant factor VIII was prepared according to the method described under Experimental. The solutions were stored at two different temperatures, 7 and 25° C., respectively.

The dispensed volume of the vials was 2 ml.

TABLE 2

| | 2A | 2B |
|---|---|---|
| Sodium chloride, M | 0.31 | 0.31 |
| Calcium chloride, mM | 3.7 | 3.7 |
| Polysorbate mg/ml | 0.23 | 0.23 |
| L-Histidine, mM | 14.7 | 59 |
| Sucrose, mg/ml | 200 | 200 |
| Glutathione mg/ml | 0.3 | — |
| Acetylcystein, mg/ml | — | 3 |
| pH | 7 | 7 |
| Headspace | $N_2$ | $N_2$ |
| VIII:C IU/ml | | |
| Initial | 105 | 108 |
| 3 months, 7° C. | 99 | 105 |
| 6 months, 7° C. | 90 | 91 |
| 2 months, 25° C. | 85 | 78 |
| 3 months, 25° C. | 78 | 66 |

Both solutions gave an acceptable stability of VIII:C after six months at 7° C.

EXAMPLE 3

Comparison Between Solutions Containing Glutathione or Ascric Acid and Stored Under Air or Nitrogen Recombinant factor VIII was prepared according to the method described under Experimental. The solutions were stored at 25° C. The dispensed volume in the vials was 2 ml.

TABLE 3

| | 3A | 3B | 3C | 3D | 3E | 3F |
|---|---|---|---|---|---|---|
| L-Histidine, mg/ml | 2.27 | 2.27 | 2.27 | 2.27 | 2.27 | 2.27 |
| Sodium chloride, mg/ml | 18.1 | 18.1 | 18.1 | 18.1 | 18.1 | 18.1 |
| Calcium chloride, mM | 3.7 | 3.7 | 3.7 | 3.7 | 3.7 | 3.7 |
| Polysorbate 80, mg/ml | 0.23 | 0.23 | 0.23 | 0.23 | 0.23 | 0.23 |
| Glutathione, mg/ml | 0 | 0 | 0.3 | 0.3 | 0 | 0 |
| Ascorbic acid, mg/ml | 0 | 0 | 0 | 0 | 4 | 4 |
| pH | 7 | 7 | 7 | 7 | 7 | 7 |
| Headspace | $N_2$ | air | $N_2$ | air | $N_2$ | air |
| VIII:C IU/ml | | | | | | |
| Initial | 231 | 231 | 225 | 225 | 220 | 220 |
| 1 months | 212 | 15 | 203 | 170 | 169 | 2 |
| 2 months | 200 | 6 | 177 | 113 | — | — |
| 3 months | 210 | — | 163 | — | — | — |

After 2 months storage under nitrogen, the factor VIII activity was retained to about 80% or more of the initial value. This was irrespective of presence or absence of glutathione. However, glutathione increased the stability considerably, when the solution was stored with air in the headspace. Ascorbic acid reduced the stability of factor VIII.

EXAMPLE 4

Comparison Between Solutions With and Without Glutathione. and Stored Under Air or Argon Recombinant factor VIII was prepared according to the method described under Experimental. The solutions were stored at two different temperatures, 7 and 25° C., respectively.

The dispensed volume in the vials was 2 ml.

TABLE 4

| | 4A | 4B | 4C | 4D | 4E | 4F |
|---|---|---|---|---|---|---|
| L-Histidine, mg/ml | 2.29 | 2.29 | 2.29 | 2.29 | 2.29 | 2.29 |
| Sodium chloride, mg/ml | 18.1 | 18.1 | 18.1 | 18.1 | 18.1 | 18.1 |
| Calcium chloride, mM | 3.7 | 3.7 | 3.7 | 3.7 | 3.7 | 3.7 |
| Polysorbate 80, mg/ml | 0.23 | 0.23 | 0.23 | 0.23 | 0.23 | 0.23 |
| Glutathione, mg/ml | — | 0.6 | 0.6 | — | 0.6 | 0.6 |
| pH | 7 | 7 | 7 | 7 | 7 | 7 |
| Storage tempertaure, ° C. | 25 | 25 | 25 | 7 | 7 | 7 |
| Headspace | Ar | Ar | air | Ar | Ar | air |
| VIII:C IU/ml | | | | | | |
| Initial | 234 | 176 | 234 | 234 | 176 | 234 |
| 1 months | 213 | 157 | 133 | 232 | 172 | 160 |
| 2 months | 187 | 139 | 90 | 200 | 153 | 148 |
| 3 months | 185 | 138 | 72 | 207 | 159 | 131 |
| 4 months | 158 | 116 | — | 186 | 144 | 125 |
| 6 months | 149 | 111 | — | 188 | 147 | 114 |
| 9 months | — | — | — | 130 | 106 | 67 |

After 6 months storage under argon, the factor VIII activity was retained to about 65% or more of the initial value after storage at 25° C. After storage at 7° C., the corresponding value was 80% or more.

We claim:

1. A formulation comprising coagulation factor VIII ready for use, wherein said factor VIII has an activity of 10 to 100,000 IU/ml in an aqueous solution with a concentration of oxygen below 200 ppm and capable of retaining at least 50% of its initial activity after storage for at least 6 months, and wherein the aqueous solution contains:
   i) 10–100,000 IU/ml of recombinant coagulation factor VIII,
   ii) at least 0.01 mg/ml of a polyoxyethylene sorbitan fatty acid ester,
   iii) sodium chloride,
   iv) calcium salt,
   v) an amino acid in an amount of more than 1 mM, and
   vi) a Mono- or disaccharide or a sugar alcohol, and is free of albumin.

2. The formulation according to claim 1, which further comprises an inert gas.

3. The formulation according to claim 2, in which the inert gas is nitrogen.

4. The formulation according to claim 1, in which the aqueous solution further contains at least one antioxidant.

5. The formulation according to claim 4, in which the antioxidant is at least one compound selected from the group consisting of glutathione, acetylcysteine and methionine.

6. The formulation according to claim 1, in which the coagulation factor VIII is full-length or a deletion derivative of recombinant factor VIII.

7. The formulation according to claim 1, in which the concentration of active coagulation factor VIII is 50 to 10,000 IU/ml.

8. The formulation according to claim 1, in which the polyoxethylene sorbitan fatty acid ester is present in an amount above the critical micelle concentration.

9. Process for preparation of the solution according to claim 1, characterised by mixing the coagulation factor VIII with an aqueous solution such that the activity is from 10 to 100,000 IU/ml, and reducing the oxygen concentration by subjecting the solution to an inert gas atmosphere.

10. Process for preparation of the formulation according to claim 1, comprising mixing the coagulation factor VIII with an aqueous solution, and reducing the oxygen concentration by first reducing the pressure and thereafter introducing inert gas.

11. The formulation according to claim 1, wherein the concentration of oxygen is below 100 ppm.

12. The formulation according to claim 11, wherein the concentration of oxygen is below 50 ppm.

13. Process according to claim 10, comprising reducing the pressure and thereafter introducing the inert gas repeatedly in several cycles.

14. The formulation according to claim 1 being capable of retaining at least 80% of its initial activity after storage for at least 6 months.

15. The formulation according to claim 1 being capable of retaining at least 50% of its initial activity after storage for at least 12 months.

16. The formulation according to claim 1 being capable of retaining at least 50% of its initial activity after storage for at least 24 months.

* * * * *